United States Patent [19]

Bukusoglu et al.

[11] Patent Number: 5,439,900
[45] Date of Patent: Aug. 8, 1995

[54] METHODS AND COMPOSITIONS FOR PROVIDING ANALGESIA AND ENHANCED ANESTHESIA

[76] Inventors: Cuneyt Bukusoglu, 125 Old Mill Rd., Shrewsbury, Mass. 01545; Johann G. Thalhammer, 398 Central St., Framingham, Mass. 01701; Neil R. Krieger, 23 Lila Rd., Jamaica Plain, Mass. 02130

[21] Appl. No.: 23,793

[22] Filed: Feb. 25, 1993

[51] Int. Cl.6 ............................................. A61K 31/56
[52] U.S. Cl. ..................................................... 514/170
[58] Field of Search ......................................... 514/170

[56] References Cited

U.S. PATENT DOCUMENTS 4,056,633 11/1977 Kreb et al. ........................... 424/331

OTHER PUBLICATIONS

Selye, "Correlations Between the Chemical Structure and the Pharmacological Actions of the Steroids," *Endocrinology* 30:437–453 (1941).
Selye, "Studies Concerning the Correlation Between Anesthetic Potency, Hormonal Activity and Chemical Structure Among Steroid Compounds," *Anesth. Analg. Current Researches*, 21:41–47, (Jan.–Feb. 1942).
Selye, "The Fish Assay for the Anesthetic Effect of the Steroids," *Anesthesiology* 4:36–47 (1943).
Hart et al., "The Analgesic and Hypnotic Actions of Barbiturates," *Anesthesiology* 9:276–280 (1948).
Figdor et al., "Central Activity and Structure in a Series of Water–Soluble Steroids," *J. Pharmacol. Exp. Therapy* 119:299–309 (1957).
P'an et al., "Steroid Central Depressants," *Methods on Hormone REsearch* III:415–477 (1964).
Atkinson et al., "Action of Some Steroids on the Central Nervous System of the Mouse," *J. Med. Chem.* 8:426–432 (1965).
Gyermek et al., "Steroids. CCCX. Structure–Activity Relationship of Some Steroidal Hypnotic Agents," *J. Med. Chem.* 11:117–125 (1968).
Raisinghani et al., "Uptake of intravenously administered progesterone, pregnanedione and pregnanolone by the rat brain," *Acta Endocrinologica* 57:395–404 (1968).
Forney et al., "Toxicology of ethanol," *Ann. Rev. Pharm.*; 9:379–389 (1969).
Dundee et al., "Use of Alcohol in Anesthesia," *Anesth. Analg.* 48:665–669 (1969).
Dundee, "Intravenous Ethanol Anesthesia: A study of dosage and blood levels," *Anesth. Analg.* 49:467475 (1970).
Curry et al., "Interaction of phenobarbitone and ethanol in mice studies from dose–response curves and drug concentrations in blood," *J. Pharm. Pharmac.* 26:771–777 (1974).
Johnstone, et al., "Effects of acute and chronic ethanol administration on isoflurane requirements in mice," *Anesth. Analg.* 54:277–281 (1975).
Gyermek et al., "Steroid Anesthetics," *Anesthesiology* 42:331–344 (1975).
Phillipps, "Structure–Activity Relationships in Steroidal Anaesthetics," *J. Steroid. Biochem.* 6:607–613 (1975).
Karavolas et al., "Uptakes of [$^3$H] progesterone and $^3$H] 5α–dihydroprogesterone by rat tissues in vivo and of accumulated radioactivity: Accumulation of 5α–dihydroprogesterone by pituitary and hypothalamic tissues," *Endocrinology* 98: 164–175 (1976).
Richards et al., "Additive and Non-Additive Effects of Mixtures of Short–Acting Intravenous Anaesthetic Agents and Their Significance for Theories of Anaesthesia," *J. Pharmac.* 74:161–170 (1981).

(List continued on next page.)

Primary Examiner—José G. Dees
Assistant Examiner—Joseph M. Conrad, III
Attorney, Agent, or Firm—Bromberg & Sunstein

[57] ABSTRACT

A novel method for preparing a subject for surgery by administering to said subject a composition which contains at least one steroid, an alcohol and a vehicle which is distinct from said alcohol. It has been discovered that there is a synergistic effect between the steroid and the alcohol which increases the anesthetic effect and the analgesic effect and shortens recovery times.

28 Claims, 5 Drawing Sheets

OTHER PUBLICATIONS

Zar, *Biostatistical analysis,* 2nd ed., Englewood Cliffs: Prentice-Hall Inc., pp. 138–146 (1984).

Harris et al., "Physical properties and lipid composition of brain membranes from ethanol tolerant-dependent mice," *Molec. Pharmacol.* 25:401–409 (1984).

Suzdak et al. "Ethanol stimulates gamma-aminobutyric acid receptor mediated chloride transport in rate brain synaptosomes," *Proc. Natl. Acad. Sci. U.S.A.* 83:4071–4075 (1986).

Way et al., "Pharmacology of intravenous non-narcotic anesthetics," In: Miller, Ed., *Anesthesia,* N.Y.: Churchill Livingstone, pp. 799–835 (1986).

Majewska et al., "Steroid hormone metabolites are barbiturate-like modulators of the GABA receptor," *Science* 232:1004–1007 (1986).

Hogskilde et al., "Anaesthetic properties of pregnanolone emulsion," *Anaesthesia* 42:1045–1050 (1987).

Kavaliers et al., "Analgesic effects of the progesterone metabolite, 3α-hydroxy-5α-pregnan-20-one and possible modes of action in mice," *Brain Res.* 415:393–398 (1987).

Mendelson et al., "Sleep Induction by an Adrenal Steroid in the Rat," *Psychopharmacology* 93:226–229 (1987).

Kavaliers et al., "Alalgesic Effects of the Progesterone Metabolite, 3α-hydroxy-5α-. . . pregnan-20-one, and Possible Modes of Action in Mice," *Brain Research* 415:393–398 (1987).

Hogskilde et al., "Pregnanolone Emulsion," *Anaesthesia* 42:586–590 (1987).

Hogskilde et al., "Anaesthetic Properties of Pregnanolone Emulsion," *Anaesthesia* 42:1045–1050 (1987).

Wiebe et al., "Analgesic effects of the putative FSH-s-uppressing gonadal steroid, 3α-hydroxy-4-pregnen-20-one: Possible modes of action. " *Brain Res.* 461:150–157 (1988).

Mehta et al., "Ethanol potentiation of GABAergic transmission in cultured spinal cord neurons involves γ-aminobutyric acid$_a$-gated chloride channels," *J. Pharmacol. Exp. Ther.* 246:558–564 (1988).

Wiebe et al., "Analgesic Effects of the Putative FSH-Suppressing Gonadal Steroid, 3α-hydroxy-4α-pregnan-20-one: Possible Modes of Action," *Brain Research* 461:150–157 (1988).

Kavaliers et al., "Inhibitory Influences of Adrenal Steroid, 3α, 5α-tetrahydroxycorticosterone on Aggression and Defeat-Induced Analgesia in Mice," *Psychopharmacology* pp. 488–492 (1988).

Corssen et al., *Intravenous Anesthesia and Analgesia,* Phila.: Lea & Febiger, Chap. 11, pp. 267–280 (1988).

Dundee, "Pharmacology of intravenous anesthetics and hypnotics," In: Nunn et al., Eds., *General anesthesia,* pp. 115–134, London: Butterworths (1989).

Mok et al., "Evidence that 5α-pregnan-3α-ol-2Gone is hemetabolite responsible for progesterone anesthesia," *Brain Res.* 553:42–45 (1990).

Mok et al., "In vivo studies identify 5α-pregnan-3α-ol-20-one as an active anesthetic agent," *J. Neurochem.* 57:1296–1301 (1991).

Sutton, "A brief history of steroid anaesthesia before thesin (CT1341)," *Postgrad. Med. J.* (Jun. Suppl.) 9–13 (1992).

Paul et al., "Neuroactive steroids," *FASEB J.* 6:2311–2322 (1992).

Mok et al., "Evidence that 3α-hydroxy-5α-pregnan-2-0-one is the Metabolite Responsible for Anesthesia Induced by 5αk-pregnanedione in the Mouse," *Neuroscience Letters* 135:145–148 (1992).

Bukusoglu et al., "Ethanol Acts as an Enhancer of Steroid Anesthetic Activity in Mouse," *FASEB* 3677 (Apr. 5–9, 1992).

Editorial in *The Lancet* 340:83–84 (1992).

METHODS AND COMPOSITIONS FOR PROVIDING ANALGESIA AND ENHANCED ANESTHESIA

TECHNICAL FIELD

The present invention relates to preparing an animal subject for surgery and in particular to providing analgesia and enhanced anesthesia.

BACKGROUND OF THE INVENTION

Methods of surgery underwent a revolution when anesthetics became available that caused the patient to enter a state of reversible loss of sensation and consciousness prior to and during surgical procedures. The anesthetic thereby protects the patient against pain by causing the patient to enter a deep sleep and providing a measure of amnesia concerning events undertaken during sedation. General anesthetics cause profound loss of consciousness with varying hypnotic, analgesic and amnestic potencies (Dundee, J. W., In: Nunn, J. F., et al., eds. General Anesthesia, London: Butterworths, 1989: 115–134). (For the purposes of this disclosure and the following claims, "general anesthesia" is understood as a state of reversible loss of sensation and consciousness. Similarly, "analgesia" is understood as a state of reduced sensibility to pain, which may occur apart from loss of consciousness and loss of the sense of touch. Also similarly, "amnesia" is understood as total or partial loss of memory of events that occurred while under general anesthesia.)

Current methods of general anesthesia involve the administration of an anesthetic gas through a tube placed in the bronchial passage of the patient thereby causing a state of deep sleep. Prior to the introduction of the tube, it is desirable to administer a fast acting sleep inducing agent to minimize discomfort to the patient incurred by the introduction of a tube into the trachea. In fact, the sleeping patient, although unconscious, still responds to pain, and the patient's reaction during introduction of the tube into the trachea can make insertion difficult or impossible causing the procedure to be halted to avoid potentially lethal consequences.

Inducing agents include either barbiturates or steroids which when administered by intravenous injection, cause the patient to rapidly enter a state of deep sleep. Barbiturates are administered in relatively high doses and there is a risk of lethal effects if the dose exceeds the optimal level by a small amount. Although barbiturates are effective in inducing a deep sleep very quickly, patients may take many hours to recover to normal wakefulness. This has the undesirable effect of rendering the patient unable to leave the healthcare facility after a procedure until the effect of the barbiturates disappear even when the actual procedure is relatively short.

An alternative to barbiturates is steroid anesthetics. The potential advantages of steroid anesthetics are lack of toxicity, good overall safety and rapid elimination by liver metabolism providing rapid recovery of the patient from anesthesia. Certain hormonal steroids as well as steroid anesthetics devoid of hormonal activity were recognized to produce anesthesia in rats over 50 years ago (Selye H., et al., Anesthesiology 1943; 4: 38–47). Until today, however, their mode of action on brain function is unknown, as are the factors that cause some steroids to be more effective anesthetics then others (Mok, W. M., et al., J. Neurochem. 1991; 57:1296–1301). One important disadvantage of steroids is their poor solubility in aqueous solutions, a serious drawback in formulating the anesthetic for intravenous administration. Efforts in improving the utility of steroid anesthetics have focused on selecting maximally active steroidal structures that are free of unwanted side effects and formulating these structures in a suitable vehicle for intravenous injection.

The steroid anesthetics and other intravenously administered general anesthetics produce deep sleep, but do not produce analgesia (Dundee, J. W., 1989; Way, W. L., et al., In: Miller, R. D., ed., Anesthesia, New York: Churchill Livingstone, 1986: 799–835; Sutton, J. A., Postgrad. Med. J. (June Suppl.) 1992: 9–13; Mok, W. M., et al., 1991; Hogskilde, S. et al., Anaesthesia 1987, 42:1045–1050). It could be argued on this basis that steroids are not true general anesthetics. The question of why these anesthetics are not analgesic is of fundamental interest.

Steroids are recognized as playing a physiological role in regulating brain function although until this time, the mechanism by which these molecules work is unknown. This has prevented the development of a mechanistic approach to developing improved steroid anesthetics. Indeed, the development of anesthetics has been largely empirical requiring extensive screening of different chemical structures in animal models to determine improved anesthetic effect without detrimental side effects.

Despite the above limitations, steroids have been successfully used as inducing agents prior to general anesthesia. However, their utility could be further improved if in addition to anesthetic properties, the steroid preparations also had analgesic properties. The administration of an inducing agent having analgesic properties would facilitate the insertion of the tube for gaseous administration of a general anesthetic in a patient who would no longer feel pain that causes them to react during the procedure. An additional advantage of an anesthetic with analgesic properties would be the reduction in the dose of anesthetic required to protect the patient against pain. This would have special benefit in short but painful procedures such as correcting a dislocated shoulder where relatively deep protection against pain is required but where the procedure instantly corrects the medical condition thereby potentially enabling the patient to return home at completion of the procedure.

An additional motivation for identifying novel anesthetics results from observed side effects seen in patients using existing anesthetic formulations. For example, Althesin, a composition that initially showed promise as a first rapid acting steroid anesthetic was discovered to cause undesirable clinical side effects. This formulation consists of the steroid, alphaxalone (3-α-hydroxy-5-α-pregnane 11.20 dione mixed with a second steroid, alphadolone acetate (21-acetoxyl derivative) dissolved in Cremaphor, a biologically acceptable medium. An example of these undesirable effects include anti-analgesic properties when administered at subanesthetic doses where a transient increase in the appreciation of somatic pain is observed (Corssen, et al., Intravenous anesthesia and analgesia, Philadelphia: Lea and Febiger, 1988). It would be highly desirable to be able to reduce the dose of steroid anesthetic to obtain the required effect so that the probability of adverse side effects from the steroids would be reduced.

For the foregoing reasons, there is a need for a composition for use in preparing animal subjects for surgery that provides the maximum anesthetic effect including the ability to provide analgesia, rapidly at the minimum dose with minimal toxicity and can be safely and easily administered to the animal subject.

SUMMARY OF THE INVENTION

The present invention is directed to a method and composition that satisfies these needs. A method for preparing animal subjects (where animal subjects includes humans) for surgery having features of the present invention comprises a composition including a steroid, an alcohol and a vehicle. An effective amount of the composition is selected sufficient to exert an anesthetic effect in an animal subject where the magnitude of the anesthetic effect of the composition is greater than such an effect cumulatively achieved by all components of the composition acting separately. The effective amount of the composition is then administered to the animal subject. In accordance with another embodiment of a the invention, a composition is provided including a steroid, an alcohol and a vehicle. An effective amount of the composition is selected sufficient to exert an analgesic effect in an animal subject where the magnitude of the analgesic effect of the composition is greater than such an effect cumulatively achieved by all components of the composition acting separately. The effective amount of the composition is then administered to the animal subject.

A further embodiment of the invention is an improved method for achieving analgesia in an animal subject in preparation for surgery of the type employing the administration of a composition including an alcohol wherein the improvement comprises adding a steroid to the composition prior to its administration. A further embodiment of the invention is a composition having analgesic and anesthetic properties comprising a steroid, an alcohol and a vehicle for forming a homogeneous mixture of the steroid and the alcohol in a desired concentration.

BRIEF DESCRIPTION OF THE DRAWINGS

The foregoing aspects of the invention will be more readily understood by reference to the following detailed description taken with the accompanying drawings, in which.

DETAILED DESCRIPTION OF SPECIFIC EMBODIMENTS

The term "nocifensive response" as used here is defined as the motor response to a noxious stimulus and is used as a measure of analgesia.

The term "loss of righting response (LRR)" as used here is defined as having occurred when the mouse fails to right itself for two minutes after being placed on its back.

The term "magnitude of effect" as used here and in the claims is defined for LRR as the percentage of animals (0-100%) that exhibit LRR at a given dose of a steroid composition; and is defined for the nocifensive response as the inverse of the ability to respond to a noxious stimulus (1-4).

The term "rate of effect" as used here and in the claims is defined as the time elapsed before LRR is observed and the time elapsed before loss of nocifensive response is observed.

The term "duration of effect" as used here and in the claims is defined as the time elapsed before the nocifensive response returns to normal.

The term "animal" as used here and in the claims includes humans.

We have found that the administration by intravenous injection of an alcohol in particular, ethanol together with at least one steroid results synergistically in marked analgesia and a marked increase in hypnotic effect. Alternative routes of administration include intraperitoneal administration and administration by inhalation. Ethanol alone at these low doses was merely sedative, and steroid alone was hypnotic without any analgesic benefit.

It has been known since the earliest days of recorded history that ethanol had sedative-hypnotic properties. Unfortunately, used on its own, the lethal dose of ethanol is only slightly above the effective dose (Dundee, J. W., Anesth. Analg. 1970; 49:467-475).

Doses of ethanol that are too low to produce hypnosis or analgesia (sub-threshold) are known to enhance the actions of a range of anesthetics (Forney, R. B., et al., Ann. Rev. Pharm. 1969; 9:379-389; Curry, S. H., et al., J. Pharm. Pharmac. 1974; 26:771-777) but are not known to produce substantial analgesia.

Our observations described below demonstrate that ethanol enhances steroid hypnotic activity and are consistent with the effects of ethanol on other sedative-hypnotic drugs (Forney, R. B., et al., 1969; Curry, S. H., et al., 1974). However, the pronounced enhancement of steroid analgesia was unanticipated because steroids are not thought to induce analgesia (Sutton, J. A., Postgrad. Med. J. (June Suppl.) 1992; 9-13; Hogskilde, S. et al., 1987; Mok, W. M., et al., Brain Res., 1990; 553:42-45).

In the examples following, the interaction between ethanol and the steroid anesthetics 3α-hydroxy-5α-pregnan-20-one (3α), and progesterone (PG) is shown with respect to LRR and the nocifensive response in the mouse where LRR is used as a measure of anesthesia and the nocifensive response is used as a measure of analgesia.

In accordance with our invention, ethanol administered with steroids, both at subthreshold doses, results in a synergism that provides for the first time both significant analgesia and enhanced anesthesia of a steroid formulation. Examples for two different steroids are given below. Other steroids that are metabolites or derivatives of metabolites of progesterone, testosterone and deoxycorticosterone may be used in combination with ethanol to obtain enhanced anesthetic and analgesic effects. Metabolites of progesterone include 3α-hydroxy-5α-pregnan-20-one, 3α-hydroxy-5β-pregnan-20-one, 5α-pregnane-3,20-dione, 5β-pregnane-3,20-dione and 5α-pregnane -3,20-diol and derivative of a metabolite of progesterone include alphaxolone, 3β-methyl-alphaxalone, 2β-methyl-alphaxalone, 2α-chloro-alphaxalone, 21α-fluoro-alphaxalone and 17β-ethyl-allopregnanolone. Metabolites of deoxycorticosterone include 21-hydroxy-5β-pregnane 3,20 dione, 3α,21α-dihydroxy-5β-pregnan 20-one and 3β,21α-dihydroxy-5β-pregnan-20-one, deoxycorticosterone acetate, and 3-succinate derivatives. Metabolites of testosterone include 5α-androstan-17β-ol-3-one and 5α-androstan-17β-3α-diol and derivatives of this metabolite include testosterone propionate.

These results call attention to a remarkable problem in behavioral pharmacology that can occur when sub-threshold activates are present, i.e., negative result with a drug injected alone does not suffice to rule out the possibility of a major contribution to activity when that drug and a second drug of interest are injected together. The experimental protocol and results in experimental animals are provided below.

EXAMPLES

1. Methods.

Mice (male albino CD-1; 18–20 g) were obtained from Charles River Breeding Laboratories (Wilmington, Mass.). 3α, PG and Cremaphor EL (CR) were obtained from Sigma (St. Louis, Mo.). Ethanol (200 proof) was obtained from Pharmco Products, Inc. (Bayonne, N.J.).

Mice were immobilized in a transparent animal holder, (General Medical Engineering Corp., MA). All injections of steroids (3α or PG) and ethanol were made i.v. in a Cremaphor saline (20%, v/v) vehicle through a tail vein.

The preparation of Cremaphor-saline delivery vehicles required procedures to take account of the relative immiscibility of the solvents with the steroid. Ethanol was used to prepare homogeneous steroid vehicles. The final vehicle (300 µl) contained 4 and 9% of ethanol which corresponded to doses of 0.5 and 1.1 g/kg bodyweight.

Vehicle without ethanol, steroid suspension in CR-saline was sonicated (Branson 1200 sonicator; Danbury, Conn.) for 15–70 seconds to form a fine suspension, then heated in a water bath at approximately 80° C. until the phase transition of CR occurred. Then, without delay, the vial was vortexed until the suspension became clear.

Vehicle with 0.5 g/kg animal (4.3 g/100 ml) dose of ethanol, was prepared according to Mok, W. M., et al., 1991. The concentration of ethanol was determined with the aid of [$^{14}$C] ethanol (NEN, Boston, Mass.).

Vehicle with 1.1 g/kg animal (7.15 g/100 ml) dose of ethanol, 1 ml of CR-saline was mixed with 1.8 ml of steroid in ethanol. Then 2 ml of CR-saline was added, vortexed and evaporated in a 70° C. water bath with horizontal air stream. The volume was adjusted to 5 ml with CR-saline. Cremaphor is an oil based vehicle that forms an emulsion with steroid and ethanol thereby providing a suitable formulation for intravenous injection. Other formulations may be used depending on the route of administration (intraperitoneal or by inhalation) and on the type of steroid in the composition.

While two doses of ethanol (0.5 g/kg and 1.1 g/kg animal) were used in these examples, it is expected that any dose less than 2.0 gm/kg animal (13 g/100 ml) will have utility in this method.

Loss of righting response (LRR) occurred when the mouse failed to right itself for two minutes after being placed on its back. When LRR did not occur within 20 minutes the mouse was scored as no LRR. Return of the righting response (RRR) was defined as having occurred when the mouse spontaneously righted itself following LRR.

Response to clamping the tail with a small hemostat, at an intensity which induced a reliable nocifensive response under control conditions, was monitored. Care was taken to avoid obvious tissue damage which might result in hyperalgesia. The hemostat was applied at consecutive sites along the tail starting at the distal end. At no time was the tail clamped twice at the same site.

Figure 1:
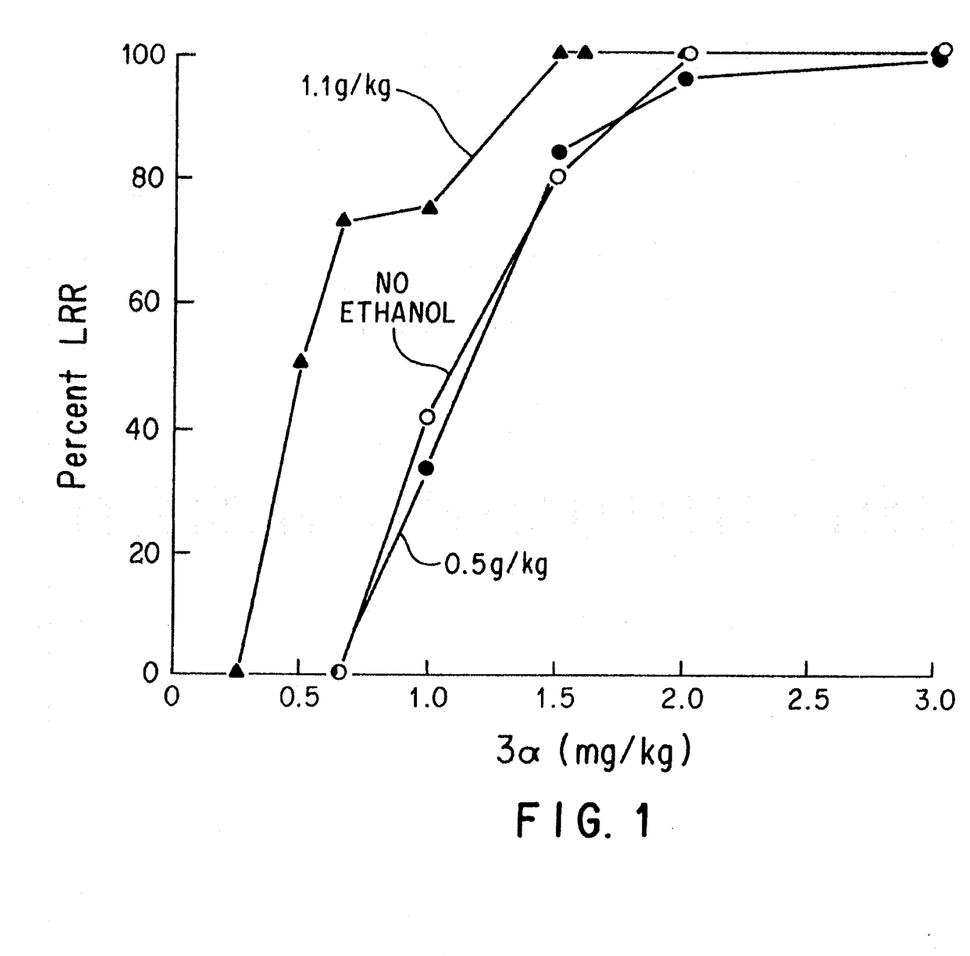
FIG. 1 plots the percentage of mice exhibiting loss of righting response (LRR) when 3α-hydroxy-5′-pregnan-20-one (3α) was administered alone or with ethanol.
Figure 2:
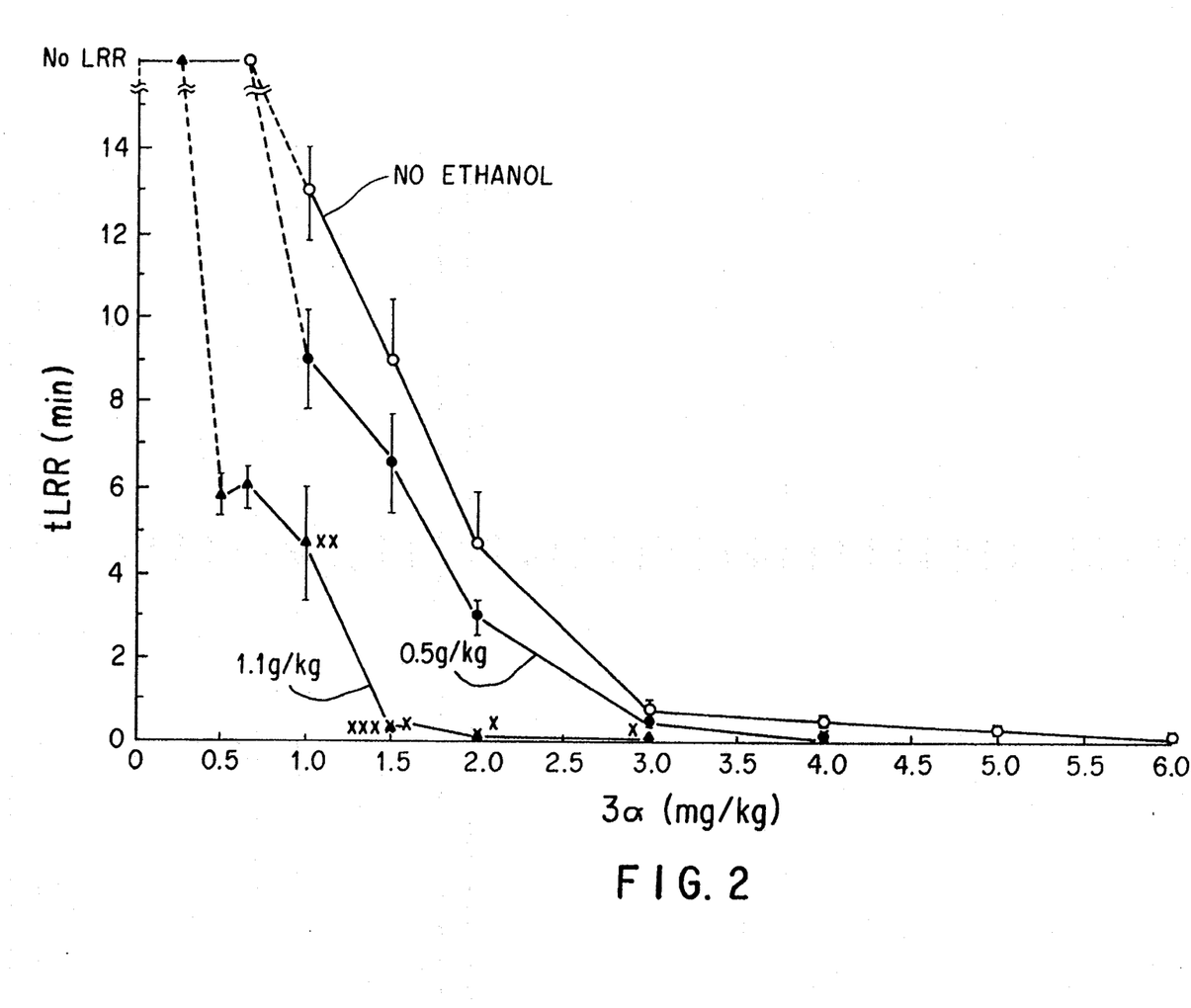
FIG. 2 plots the effect of ethanol on the time to the loss of the righting response (tLRR) demonstrating the rate of effect.
Figure 3A:
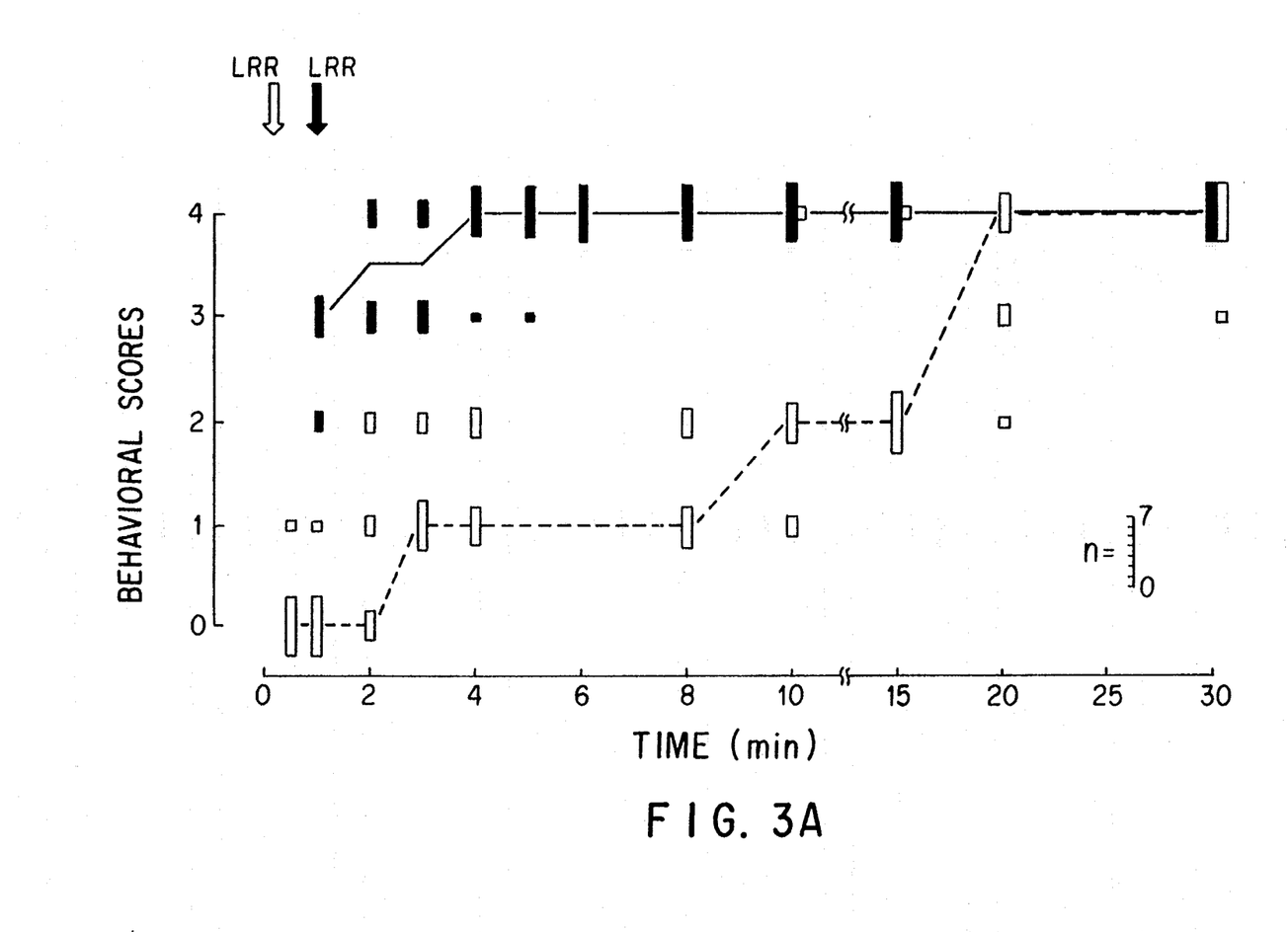
FIG. 3A plots the time course of nocifensive response to tail clamp following injection of 3α (3 mg/kg) with (□) or without ethanol (1.1 g/kg) (■)

It is difficult to evaluate analgesia in an animal that has lost the righting response. Thus we have chosen to quantitate the motor response to a noxious stimulus (nocifensive response) as a measure of analgesia. The response to stimulation of the tail was graded from 0 to 4:0=no response; 1=movement of body without limb movement; 2=lim movement; 3=jumping/squeaking; 4=jumping/running. Where O corresponds to "analgesia"; 1 corresponds to moderate analgesia; 2–3 corresponds to mild analgesia, and 4 to no analgesia. The full nocifensive response was defined as score 4. CR-saline. (20/80, V/V) was not itself anesthetic, it produced neither LRR nor any analgesia. The Student t test was used to evaluate the significance of the difference between means (FIG. 2) (Zar, J. H., Biostatistical analysis, 2nd Ed., Englewood Cliffs: Prentice-Hall Inc., 1984: 138–146). The Mann-Whitney test (two-sample rank testing) was used to evaluate the significance of the difference between two non-parametric groups (FIG. 1 and FIG. 3A). In this test the data are ranked and the comparison is made between the ranks of the measurements (Zar, J. H., 1984).

2. Results.

3α-hydroxy-5α-pregnan-20-one was administered to mice with and without ethanol. FIG. 1 plots the percentage of mice exhibiting loss of righting response (LRR) when 3α-hydroxy-5α-pregnan-20-one (3α) was administered alone or with ethanol [(0.5 or 1.1 g/kg), n≧5] at different concentrations of steroid. The percentage of mice that showed LRR was increased for steroid in the presence of ethanol at a given concentration compared with either steroid on its own or steroid in reduced concentrations of ethanol. This shows that the magnitude of effect of a steroid and ethanol composition on LRR varies according to the ratio of steroid to ethanol and is not an additive effect. FIG. 2 plots the effect of ethanol on the time to the loss of the righting response (tLRR)(min; mean±SEM). In FIG. 2, 3α was administered alone or with ethanol (0.5 or 1.1 g/kg), n≧5, *P<0.05,  P<0.01, * P<0.001 as compared to control (o) (two-tailed student t-test). The percentage of mice that reached LRR and the corresponding time of effect (tLRR) are shown as functions of the dose of 3α. In the absence of ethanol ED$_{50}$ for 3α was 1.05 mg/kg (FIG. 1). With 1.1 g ethanol/kg, ED$_{50}$ for 3α was 0.5 mg/kg. The values for percent LRR were compared over the entire dosage of 3α for the conditions with and without 1.1 g/kg ethanol. The values with ethanol were significantly higher (p<0.025 One tailed-Mann Whitney Test) (Zar, J. H., 1984). Ethanol alone resulted in less than 10% LRR. Ethanol 2 g/kg i.v. caused LRR 100. Values for tLRR were markedly reduced with 1.1 g/kg ethanol as compared to those with 0.5 g/kg or without ethanol (FIG. 2).

Figure 3B:
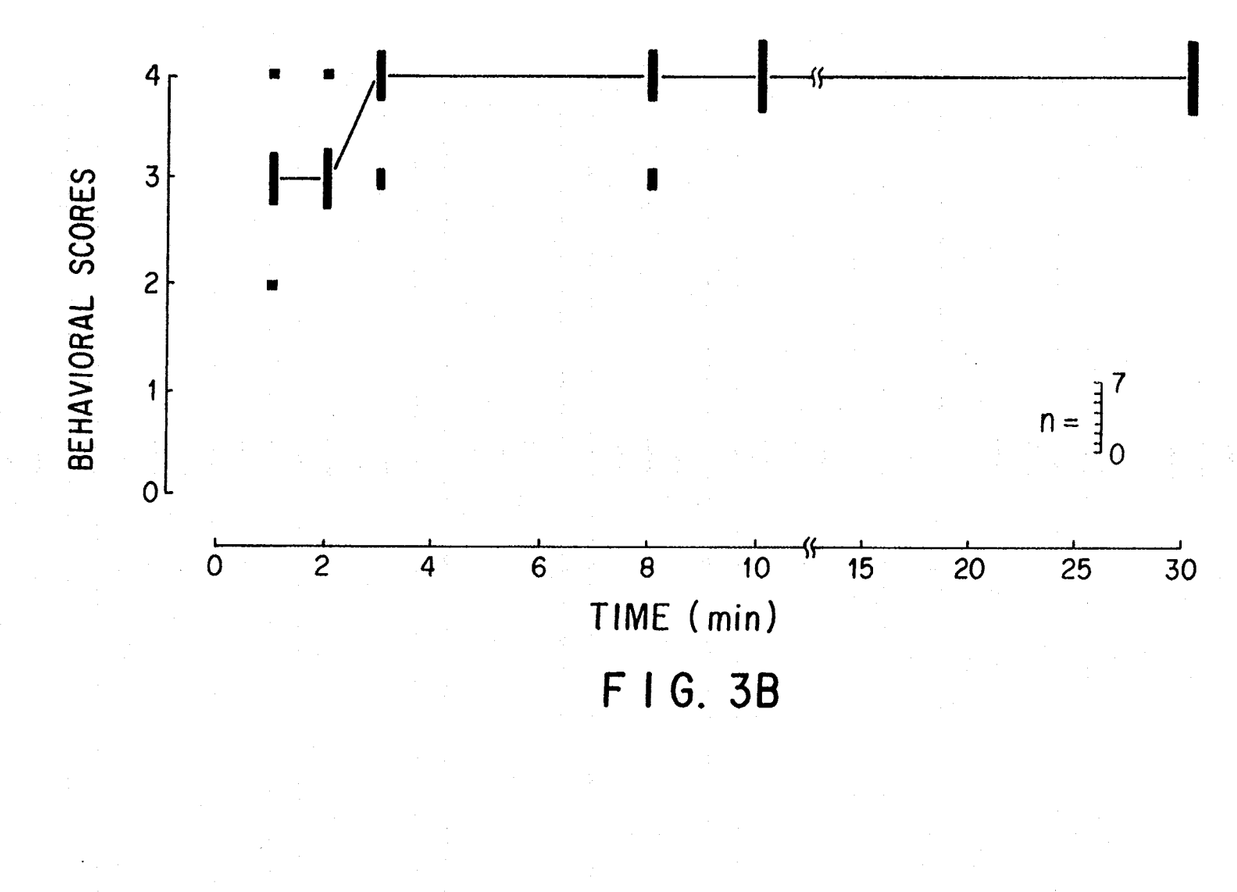
FIG. 3B plots the time course of nocifensive response to tail clamp following injection of ethanol alone.

As shown in FIG. 3, behavioral scores over the entire observation period for 3α injected with ethanol were significantly lower than the scores for 3α injected without ethanol. FIG. 3A plots the time course of nocifensive response to tail clamp following injection of 3α (3 mg/kg) with (□) or without ethanol (1.1 g/kg) (■),(P<0.025 One tailed-Mann Whitney test) (Zar, J. H., 1984). (The bar height indicates the number of times a particular score was assigned. Lines connect the median values of behavioral scores. Measurements of analgesia followed the onset of LRR.) The duration of effect was found to be as follows: 3α (3 mg/kg) with ethanol (1.1 g/kg) abolished the nocifensive response ("analgesia", behavioral score 0) for the first two minutes. LRR occurred within 10 seconds. From 3 to 8 min the median score was increased to 1; at 10 min the score was 2; at 20 min, the median score was 4 and at 30 min an analgesic effect was no longer evident. In contrast, as shown in FIG. 3A, following the injection of 3α alone, the median response to tail clamp was 3 at 1 min and 4 at 4 min. LRR occurred at 0.91±0.2 min. (mean±SEM). At no time was "analgesia" observed. Following the injection of ethanol alone the analgesic response was initially observed to be 3 and then 4 at 3 min, as shown in FIG. 3B. In FIG. 3B, ethanol alone in its Cremaphor vehicle was injected at 1.1 g/kg (n=7). Analgesia and LRR were not observed.

Figure 4:
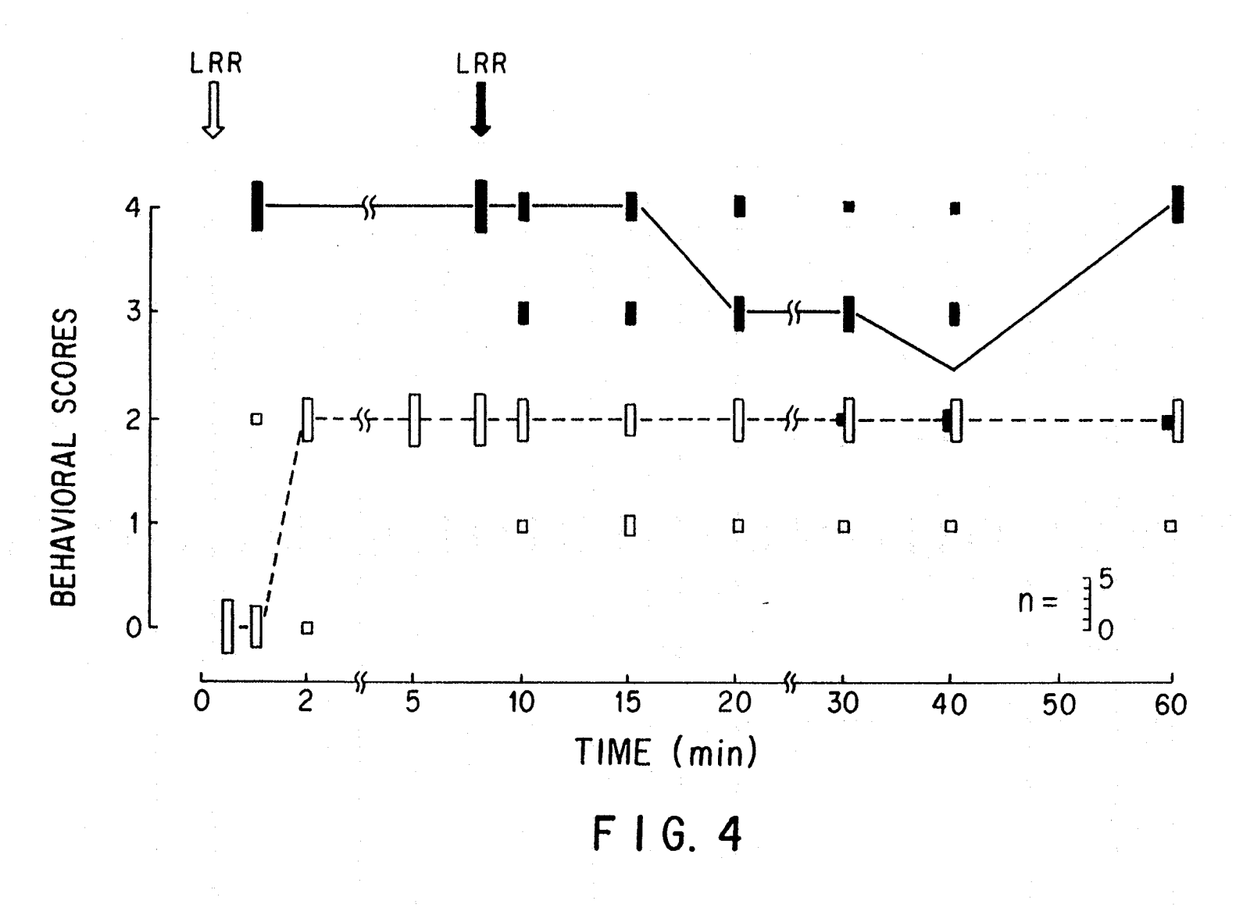
FIG. 4 plots the time course of nocifensive response to tail clamp following injection of PG (80 mg/kg) with (□, n=5) or without ethanol (1.1 g/kg) (■, n=5).

PG (80 mg/kg) with ethanol (1.1 g/kg) abolished the nocifensive response within the first minute, as shown in FIG. 4. FIG. 4 plots the time course of nocifensive response to tail clamp following injection of PG (80 mg/kg) with (□, n=5) or without ethanol (1.1 g/kg) (■, n=5). (The bar height indicates the number of times a particular score was assigned. Lines connect the median values of behavioral scores. Open and filled arrows (LRR) (time, mean) refer to mice that received ethanol and did not receive ethanol, respectively.) LRR occurred within 10 seconds. From 2-60 min the mice showed a median response of 2. Following the injection of PG alone, there was no evidence of analgesia for up to 8 min. At 20 min following injection, the median response was 3 and it returned to 4 by 60 min. PG at a lower dose of 20 mg/kg in the presence of 1.1 g/kg ethanol did not result in analgesia (not shown). PG (80 mg/kg) alone led to LRR within 8±0.8 min (mean±SEM). For all the mice that received PG, LRR occurred at times greater than 60 min. The production of 3α is probably responsible for this sustained phase (Mok, W. M., et al., 1990; Raisinghani, K. H., et al., Acta Endocrinologica 1968; 57:395-404; Karavolas, H. J., et al., Endocrinology 1976; 8:164-175.

In mice injected with 3α alone, nocifensive behavior fully returned (score=4) before the mouse regained the righting response (Table 1). Ethanol alone did not induce LRR for up to 30 min. It did induce a transient, mild analgesic response for 3.8±1 min. When 3α was co-injected with ethanol the recovery of nocifensive behavior was delayed and coincided with RRR. Furthermore, the motor activity during the nocifensive response at RRR was well coordinated and the gait was quite normal as soon as RRR occurred. With 3α (9 mg/kg), LRR occurred rapidly, the nocifensive response was mild and returned to score 4 before RRR. With 3α alone (3-9 mg/kg) following LRR, the nocifensive response was vigorous, but proper motor coordination was lacking.

Concentrations of steroids required to provide optimum effect in the presence of alcohol vary according to the type of steroid used. Indeed doses of progesterone used were about 27 fold higher than that of 3α. It is expected however that doses in the range and not exceeding 150 mg steroid/kg animal (1 gm/100 ml) will have utility in the presence of ethanol for enhancing the anesthetic and analgesic effect of the composition using the method of the invention.

***

PG and 3α are each rapidly converted to metabolites (Mok, W. M., et al., 1991; Mok, W. M., et al., 1990; Karavolas, H. J., et al., 1976). However, metabolites seem unlikely to be responsible for the observed activities with ethanol since these activities occurred within 30s following injection when metabolite formation is virtually nil (Mok, W. M., et al., 1991; Raisinghani, K. H., et al., 1968). Therefore, it is PG (FIG. 4) and 3α (FIG. 3) that mediate analgesia and LRR.

This report is the first in which PG itself has been shown to have anesthetic properties. The slower onset of mild analgesia 15-20 min following the injection of PG without ethanol paralleled the time course for the formation of 3α from PG in vivo (Mok, W. M., et al., 1990; Raisinghani, K. H., et al., 1968; 57:395-404; Karavolas, H. J., et al., 1976) and is consistent with the hypothesis that analgesia is due to the production of 3α.

Since 3α is a potent hypnotic, the onset of LRR might have precluded observations of a nocifensive response. Although steroid alone did induce LRR, it never fully abolished nocifensive behavior. Co-injection of steroids and ethanol induced analgesia which lasted as long as LRR; and as soon as the animal responded to tail clamping the motor response was well coordinated. Thus steroids plus ethanol not only alter the information needed to induce the righting response resulting from non-noxious stimulation, but also alter the information leading to nocifensive behavior.

Using changes in tail flick latency (Kavaliers, M., et al., Brain Res. 1987; 415:393-398; Wiebe, J. P., et al., Brain Res. 1988; 461:150-157) have shown a mild analgesic effect by 3α and PG intracranially injected in a 100% ethanol vehicle. Interestingly, in contrast to the rapid onset of analgesia in the present experiments, they observed a long lag period (15-60 min) before onset. LRR did not occur in their experiments. Although their ethanol vehicle lacked analgesic activity when administered alone, our results support the possibility that ethanol did contribute to the analgesic response that they observed.

At present, it is unclear what the mechanism of interaction is between alcohol and steroids. One possible target is the $GABA_A$ receptor chloride channel complex for the hypnotic actions of steroids. The marked difference in the potencies of PG and 3α in the behavioral assay for analgesia indicates that the target site is specific with respect to steroid structure. Specificity constitutes additional evidence for a receptor hypothesis. We suggest that the $GABA_A$ receptor may also mediate the analgesic actions of steroids.

As demonstrated here, steroids in combination with ethanol constitute a general anesthetic with both analgesic and hypnotic properties.

Although certain preferred embodiments of the present invention have been described, the spirit and scope

TABLE 1

|  | tLRR | tRRR | tRNR | n |
|---|---|---|---|---|
| 3α (3 mg/kg) = | 0.91 ± 0.2 | 12 ± 2 | 3.2 ± 1 | 6 |
| Ethanol (1.1 g/kg) | * | * | 3.8 ± 1 | 7 |
| 3α ± Ethanol = | 0.17 ± 0.01 | 27 ± 6 | 27.0 ± 6 | 7 |
| 3α (9 mg/kg) = | 0.17 ± 0.01 | 25 ± 6 | 9.0 ± 5 | 3 | tLRR = time to Loss of the righting response
tRRR = time to Return of the righting response
tRNR = time to return of the full nocifensive response (behavioral score 4)
t = time in minutes after injection (mean ± SEM)
* = did not occur
n = number of mice

What is claimed is:

1. A method for preparing an animal subject for surgery comprising:
   (a) providing a composition including at least one steroid, an alcohol and a vehicle distinct from the alcohol, the amount of alcohol in relation to the steroid being effective to provide, in a suitable dose of the composition, an enhanced anesthetic effect in comparison to that of the steroid itself;
   (b) selecting an effective amount of the composition sufficient to exert an anesthetic effect in an animal subject such that the magnitude of the anesthetic effect of the composition is greater than such an effect cumulatively achieved by all components of the composition acting separately; and
   (c) administering the effective amount of the composition to the animal subject.

2. A method according to claim 1, wherein step (b) includes the step of selecting an effective amount of the composition sufficient to achieve a rate of effect for anesthesia of the composition greater than the rate of effects cumulatively achieved by all components of the composition acting separately.

3. A method according to claim 1, wherein step (b) includes the step of selecting an effective amount of the composition sufficient to exert an analgesic effect together with the anesthetic effect in an animal subject such that the magnitude of at least one of the analgesic effect and the anesthetic effect of the composition is greater than such effects cumulatively achieved by all components of the composition acting separately.

4. A method according to claim 3, wherein step (b) further includes the step of selecting an effective amount of the composition sufficient to achieve a rate of effect for analgesia and anesthesia of the composition greater than the rate of effects cumulatively achieved by all components of the composition acting separately.

5. A method for preparing an animal subject for surgery comprising:
   (a) providing a composition including at least one steroid, an alcohol and a vehicle distinct from the alcohol, the amount of alcohol in relation to the steroid being effective to provide, in a suitable dose of the composition, an enhanced anesthetic effect in comparison to that of the steroid itself;
   (b) selecting an effective amount of the composition sufficient to exert an anesthetic effect in an animal subject such that the magnitude of the anesthetic effect of the composition is greater than such an effect cumulatively achieved by all components of the composition acting separately; and
   (c) administering the effective amount of the composition to the animal subject.

6. A method according to claim 5, wherein step (b) includes the step of selecting an effective amount of the composition sufficient to achieve a duration of effect for analgesia of the composition being greater than the rate of effects cumulatively achieved by all components of the composition acting separately.

7. A method according to claim 1, wherein the steroid is an endogenous steroid.

8. A method according to claim 7, wherein the endogenous steroid is selected from the group consisting of progesterone, testosterone and deoxycorticosterone.

9. A method according to claim 7, wherein the steroid is a metabolite of progesterone.

10. A method according to claim 9, wherein the steroid is selected from a group consisting of 3α-hydroxy-5α-pregnan-20-one, 3α-hydroxy-5β-pregnan-20-one, 5α-pregnane-3,20-dione, 5β-pregnane-3,20-dione and 5α-pregnane -3,20-diol.

11. A method according to claim 10, wherein the steroid is a derivative of a metabolite of progesterone.

12. A method according to claim 11, wherein the steroid is selected from a group consisting of alphaxolone, 3β -methyl-alphaxalone, 2β-methyl-alphaxalone, 2α-chloro-alphaxalone, 21α-fluoro-alphaxalone and 17β-ethyl-allopregnanolone.

13. A method according to claim 7, wherein the steroid is a metabolite of deoxycorticosterone.

14. A method according to claim 13, wherein the steroid is selected from the group consisting of 21-hydroxy-5β-pregnane 3,20 dione, 3α, 21α-dihydroxy-5β-pregnan 20-one, 3β,21α-dihydroxy-5β-pregnan-20-one and deoxycorticosterone acetate.

15. A method according to claim 14, wherein the steroid is a derivative of the metabolite of deoxycorticosterone.

16. A method according to claim 14, wherein the steroid is 3-succinate derivative.

17. A method according to claim 7, wherein the steroid is a metabolite of testosterone.

18. A method according to claim 17, wherein the steroid is selected from the group consisting of 5α-androstan-17β-ol-3-one and 5α-androstan-17β-3α-diol.

19. A method according to claim 18, wherein the steroid is a derivative of the metabolite of testosterone.

20. A method according to claim 19, wherein the steroid is testosterone propionate.

21. A method according to claim 1, wherein the alcohol is ethanol.

22. A method according to claim 21, wherein the step of selecting an effective amount of the composition is conducted so as to result in a dosage of ethanol that is less than 2 g/kg of body weight of the animal subject.

23. A method according to claim 7, wherein the step of selecting an effective amount of the composition is conducted so as to result in a dosage of steroid that is less than 150 mg/kg of body weight of the animal subject.

24. A method according to claim 1, wherein step (c) includes the step of administering the composition by one of intravenous, intraperitoneal and inhalation methods.

25. A method according to claim 1, wherein the composition is a homogeneous mixture.

26. A method according to claim 1, wherein the vehicle contains an oil suitable for intravenous injection of the composition.

27. A method according to claim 26, wherein the oil is Cremaphor and the vehicle is Cremaphor saline.

28. An improved method for achieving analgesia in an animal subject in preparation for surgery of the type employing the administration of a composition including an alcohol wherein the improvement comprises adding at least one steroid to the composition prior to its administration.

* * * * *